April 20, 1954 H. C. SWIM Plant Pat. 1,269
ROSE PLANT
Filed March 17, 1953
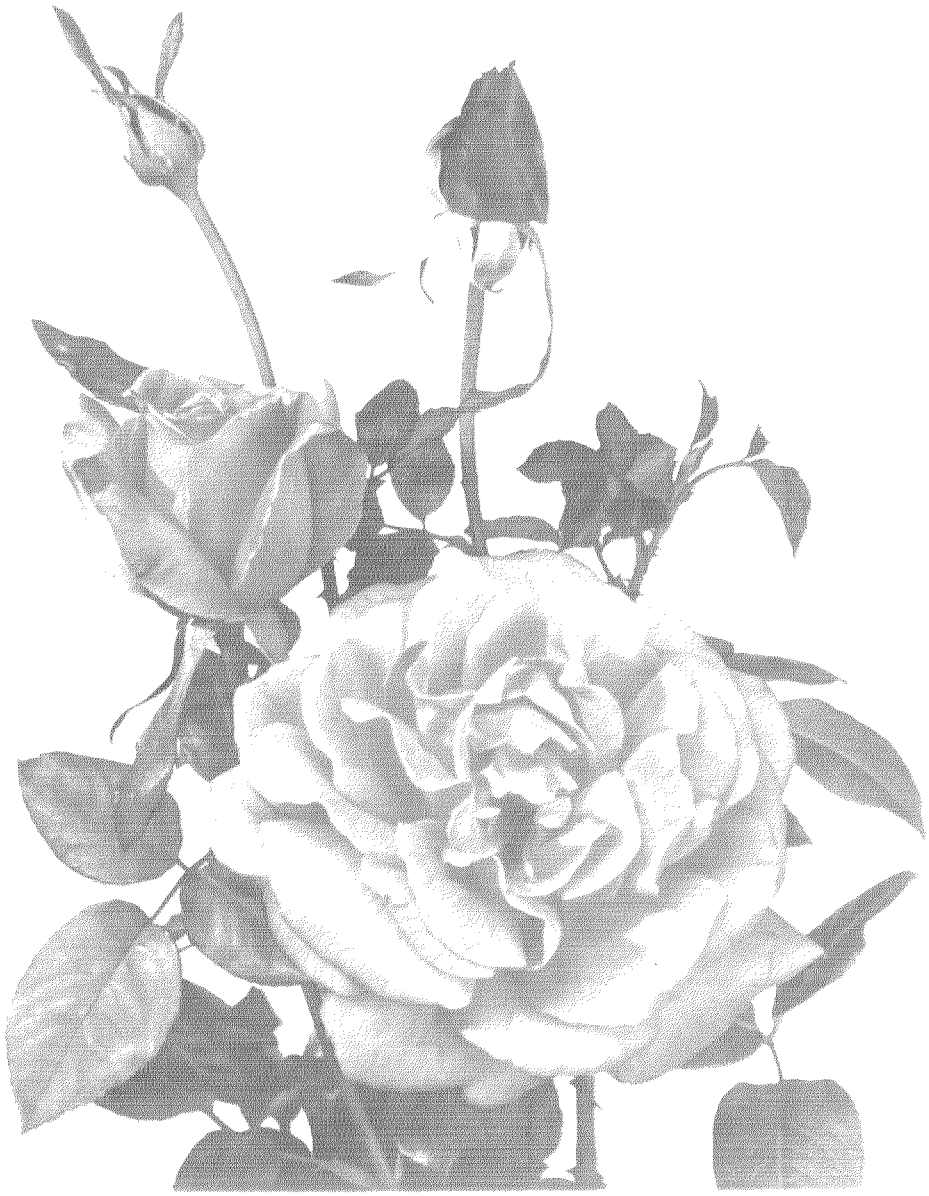
Inventor.
H. C. Swim
By: Robert Cobb
Attorneys.

Patented Apr. 20, 1954 Plant Pat. 1,269

UNITED STATES PATENT OFFICE 1,269

ROSE PLANT

Herbert C. Swim, Ontario, Calif., assignor, by mesne assignments, to Arp Nursery Company, Tyler, Tex., a partnership Application March 17, 1953, Serial No. 343,010

1 Claim. (Cl. 47—61)

The present invention relates to a new and distinct variety of rose plant of the hybrid tea class, which was originated by me by crossing the well-known variety "Charlotte Armstrong" (Plant Patent No. 455) with the variety "Texas Centennial" (Plant Patent No. 162).

The primary objective in making this cross was to produce a new variety of rose plant which combines the best characteristics of the two parent varieties. This objective was fully achieved, as evidenced by the fact that my new variety is particularly and importantly characterized by the large size of its blooms (which is a characteristic of both parents); by the regular formation of its blooms (which is a characteristic of the seed parent "Charlotte Armstrong"); by the relatively strong fragrance of the blooms (which is a characteristic of the pollen parent "Texas Centennial"); and by the good petal substance of its blooms, with attendant long-lasting quality thereof (as is typical of "Texas Centennial").

In comparison with its seed parent "Charlotte Armstrong," my new variety is definitely distinguished therefrom by the fact that the blooms of the new variety are a light to medium shade of pink color, whereas those of "Charlotte Armstrong" are deep pink in color and are more popularly described as Spectrum Red to Cerise; the buds of my new variety are ovoid to broadly ovoid in shape, whereas those of "Charlotte Armstrong" are long-pointed to long urn-shaped; and the blooms of my new variety have a strong fragrance, whereas those of "Charlotte Armstrong" have only a slight fragrance.

As compared with its pollen parent "Texas Centennial," the light to medium pink blooms of my new variety are quite distinct from the light red blooms of this parent; the foliage of my new variety is substantially larger in size than that of this parent; and the flowers of my new variety have many more petals than do those of "Texas Centennial," the petalage of the flowers of my new variety averaging from 38 to 45 in number as compared with 16 to 25 petals of the semi-double blooms of "Texas Centennial."

Asexual reproduction of my new variety by budding at Ontario, California, shows that the foregoing characteristics and distinctions come true to form and are established and transmitted through succeeding propagations.

The accompanying drawing shows typical specimens of the flowers, stems and foliage of my new variety, with the colors thereof depicted as nearly true as it is possible to make the same in an illustration of this character.

The following is a detailed description of my new variety, with color terminology in accordance with Robert F. Wilson's Horticultural Colour Chart (hereinafter identified as "Wilson") and Ridgway's Color Standards and Nomenclature (hereinafter identified as "Ridgway"):

Type: Bush; outdoor; seedling; for cut flowers and for garden decoration.

Class: Hybrid tea.

Breeding: Seedling.

*Seed parent.*—"Charlotte Armstrong."

*Pollen parent.*—"Texas Centennial."

Propagation: Holds its distinguishing characteristics through succeeding propagations by budding.

*Flower*

Locality where grown and observed: Ontario, California.

Flowers borne: Usually singly, but sometimes 3 to 4 to stem; on normal strength, medium to long stems.

Quantity of bloom: Free, outdoors.

Continuity: Nearly continuous during growing season.

Fragrance: Strong; damask.

Bud:

*Peduncle.*—Average length; average caliper; erect; smooth; some gland-tipped cilia. Color—between Lettuce Green, Plate V (Ridgway) and Parrot Green, Plate VI (Ridgway).

*Before calyx breaks.* — Size — medium. Form—medium length; ovoid; with foliaceous appendages, glabrous on the surface of the bud; usually with stout, much-cut foliaceous parts extending beyond the tip of the bud equal to about ¼ of its length.

*As calyx breaks.*—Color—between Orient Red, Plate 819, page 165 (Wilson) and Blood Red, Plate 820, page 166 (Wilson).

*Sepals.*—Inner surface—with fine, woolly tomentum. Margins—margins of alternate sepals lined with fine, woolly tomentum; others lined with stipitate glands and some hairs.

*As first petal opens.*—Size—average to large. Form—medium length; ovoid to broadly ovoid. Color—outside: between Carmine, Plate 21/2, page 21 (Wilson) and Crimson, Plate 22/2, page 22 (Wilson), with small area at base of petal near attachment near Aureolin, Plate 3/2, page 3 (Wilson); inside: between Carmine, Plate 21/1, page 21 (Wilson) and Crimson, Plate 22/1, page 22

(Wilson), with small area at base of petal near attachment near Aureolin, Plate 3/1, page 3 (Wilson). Opening—opens up well; is not retarded from opening by cold, hot, wet or dry weather.

Bloom:

*Size, when fully open.*—Large; 4 inches to 5 inches.

*Petalage.*—Double; from 38 to 45 petals, plus 8 to 14 petaloids; arranged regularly.

*Form.*—High-centered at first; becoming open to somewhat cupped; petals being at first somewhat flat-cupped, with lateral margins reflexed ⅓ to ½ of upper portion of petal, and with apex sometimes slightly reflexed for ¼ of length of petal; becoming later at maturity, flat, with lateral margins reflexed slightly ½ to ¾ of upper portion of petal, and with apex sometimes reflexed for ⅓ of length of petal.

Petals:

*Texture.*—Thick, leathery; with inside somewhat velvety and outside shiny to satiny.

*Shape.*—Outside—broadly obovate, with apex flat and usually with 1 to 2 notches. Intermediate—obovate, with apex rounded to flat and with 1 to 2 notches. Inside—obovate; somewhat irregular, with apex rounded and with 1 to 2 or more notches.

This description of a newly opened flower was made from a rose grown outdoors in the month of September, at Ontario, California.

*Color.*—Outside petal—outside surface: between Carmine, Plate 21/2, page 21 (Wilson) and Crimson, Plate 22/3, page 22 (Wilson), with small area at base of petal near attachment near Aureolin, Plate 3/2, page 3 (Wilson); inside surface: between Crimson, Plate 22/1, page 22 (Wilson) and Rose Madder, Plate 23/2, page 23 (Wilson), with small area at base of petal near attachment near Aureolin, Plate 3/1, page 3 (Wilson). Intermediate petal — outside surface: between Carmine, Plate 21/2, page 21 (Wilson) and Crimson, Plate 22/3, page 22 (Wilson), with small area at base of petal near attachment near Aureolin, Plate 3/1, page 3 (Wilson); inside surface: between Carmine, Plate 21/1, page 21 (Wilson) and Crimson, Plate 22/2, page 22 (Wilson), with small area at base of petal near attachment near Aureolin, Plate 3/1, page 3 (Wilson). Inner petal—outside surface: between Carmine, Plate 21/2, page 21 (Wilson) and Crimson, Plate 22/2, page 22 (Wilson), with small area at base of petal near attachment near Aureolin, Plate 3/1, page 3 (Wilson); inside surface: between Carmine, Plate 21/1, page 21 (Wilson) and Crimson, Plate 22/2, page 22 (Wilson), with small area at base of petal near attachment near Aureolin, Plate 3/1, page 3 (Wilson).

This description was made from a rose that was open for three days outdoors in the month of September, at Ontario, California:

*Color.*—Outside petal—outside surface: between Crimson, Plate 22/3, page 22 (Wilson) and Rose Madder, Plate 23/3, page 23 (Wilson), with small area at base of petal near attachment near Canary Yellow, Plate 2/3, page 2 (Wilson); inside surface—near Rose Madder, Plate 23/3, page 23 (Wilson), with small area at base of petal near attachment near Canary Yellow, Plate 2/3, page 2 (Wilson). Inside petal—outside surface: between Rose Madder, Plate 23/2, page 23 (Wilson) and Rose Madder, Plate 23/3, page 23 (Wilson), with small area at base of petal near attachment near Canary Yellow, Plate 2/3, page 2 (Wilson); inside surface: between Rose Madder, Plate 23/2, page 23 (Wilson) and Rose Madder, Plate 23/3, page 23 (Wilson), with small area at base of petal near attachment near Canary Yellow, Plate 2/3, page 2 (Wilson).

*General color effect.*—Newly opened flower—between Carmine, Plate 21/2, page 21 (Wilson) and Crimson, Plate 22/2, page 22 (Wilson). Three days open — between Rose Madder, Plate 23/2, page 23 (Wilson) and Rose Madder, Plate 23/3, page 23 (Wilson), with small area at base of petal near attachment near Canary Yellow, Plate 2/3, page 2 (Wilson).

*Behavior.*—Drop off cleanly; not particularly affected by cool, hot, wet or dry weather.

*Flower longevity.*—On bush in garden—3 to 4 days in September. Cut roses grown outdoors kept at living-room temperatures—3 days in September.

*Reproductive organs*

Stamens: Average number; arranged regularly about pistils.

Filaments: Medium length; 7 to 10 mm. in length; most with anthers. Color—near Canary Yellow, Plate 2/3, page 2 (Wilson).

Anthers: Medium size; all open approximately at once. Color—upper side: near Empire Yellow, Plate 603/3, page 66 (Wilson), with margin near Indian Yellow, Plate 6/2, page 6 (Wilson); under side: near Empire Yellow, Plate 603/3, page 66 (Wilson), with margin near Indian Yellow, Plate 6/2, page 6 (Wilson).

Pollen: Moderate to abundant. Color—near Indian Yellow, Plate 6/2, page 6 (Wilson).

Pistils: Many; approximately 90 in number.

Styles: Even; average length; average caliper; bunched. Color—near Sap Green, Plate 62/3, page 62 (Wilson) toward ovary and near Scarlet, Plate 19/1, page 19 (Wilson) toward stigma.

Stigma: Color—between Aureolin, Plate 3/3, page 3 (Wilson) and Lemon Yellow, Plate 4, page 4 (Wilson).

Ovaries: Most enclosed in calyx but some protruding from calyx.

Hips: Average length; globular, with inconspicuous neck; smooth; walls thick and fleshy. Color (half mature)—near Lettuce Green, Plate V (Ridgway).

Sepals: Permanent; medium-length; recurved. Color—inside: near Parrot Green, Plate VI (Ridgway), masked with white tomentum; outside: near Parrot Green, Plate VI (Ridgway).

Seeds: Few; usually medium size; from 8 to 12 in number.

*Plant*

Foliage:

*Leaves.*—Compound of usually 5 to 7 leaflets: normal quantity; medium size; heavy; leathery and glossy.

*Leaflets.*—Shape—ovoid, with acute apex and round base. Margin—simply serrate.

*Color.*—Mature—upper surface: between Deep Dull Yellow-Green, Plate XXXII (1) (Ridgway) and Dark Dull Yellow Green, Plate XXXII (Ridgway); under surface: between Courge Green, Plate XVII (Ridgway) and Biscay Green, Plate XVII (Ridgway). Young—upper surface: between Lettuce Green, Plate V (Ridgway) and Spinach Green, Plate V (Ridgway), shaded with near Dark Corinthian Purple, Plate XXXVIII (Ridgway); under surface: between Vernonia Purple, Plate XXXVIII (Ridgway) and Corinthian Purple, Plate XXXVIII (Ridgway).

*Rachis (the supporting stem of the compound leaf).*—Average size. Upper side—grooved, with some stipitate glands on edges. Under side—moderately prickly and with stipitate glands.

*Stipules.*—Medium length to long; narrow to medium width; with short points turning out at an angle of less than 45°.

*Disease.*—Average resistance to mildew, as compared with other varieties grown under comparable cultural conditions at Ontario, California.

Growth:

*Habit.*—Bushy and somewhat upright; much-branched.

*Growth.*—Free to vigorous.

*Canes.*—Medium caliper.

*Main stems.*—Color—between Yellowish Oil Green, Plate V (Ridgway) and Oil Green, Plate V (Ridgway). Large prickles—many; medium length; hooked slightly downward; with medium length, somewhat narrow base. Color—between Light Drab, Plate XLVI (Ridgway) and Drab, Plate XLVI (Ridgway). Small prickles—

Several. Color—between Light Drab, Plate XLVI (Ridgway) and Drab, Plate XLVI (Ridgway). Hairs—none.

*Branches.*—Color—between Lettuce Green, Plate V (Ridgway) and Parrot Green, Plate VI (Ridgway). Large prickles—many; medium length; hooked slightly downward; with medium length, somewhat narrow base. Color—between Mikado Brown, Plate XXIX (Ridgway) and Sayal Brown, Plate XXIX (Ridgway). Small prickles—several. Color—between Mikado Brown, Plate XXIX (Ridgway) and Sayal Brown, Plate XXIX (Ridgway). Hairs—none.

*New shoots.*—Color—near Lettuce Green, Plate V (Ridgway). Large prickles—many; medium length; almost straight; with medium length, narrow base. Color—near Chrysolite Green, Plate XXXI, (Ridgway), shaded with near Deep Brownish Vinaceous, Plate XXXIX (Ridgway). Small prickles—several. Color—near Chrysolite Green, Plate XXXI (Ridgway), shaded with near Deep Brownish Vinaceous, Plate XXXIX (Ridgway). Hairs—none.

I claim:

A new and distinct variety of rose plant of the hybrid tea class, substantially as herein shown and described, characterized particularly as to novelty by the distinctive color, relatively large size, regular formation and relatively strong fragrance of its blooms, and by the good petal substance and attendant long-lasting quality of its blooms.

No references cited.